(12) United States Patent
Sahbaee Bagherzadeh et al.

(10) Patent No.: US 11,389,127 B2
(45) Date of Patent: Jul. 19, 2022

(54) SPECTRAL CT-BASED 511 KEV FOR POSITRON EMISSION TOMOGRAPHY

(71) Applicants: Siemens Healthcare GmbH, Erlangen (DE); THE UNITED STATES OF AMERICA, AS REPRESENTED BY THE SECRETARY, DEPARTMENT OF HEALTH AND HUMAN SERVICES, Bethesda, MD (US)

(72) Inventors: Pooyan Sahbaee Bagherzadeh, Mount Pleasant, SC (US); Babak Saboury Sichani, Laurel, MD (US); Faraz Farhadi, Fairfax, VA (US)

(73) Assignees: Siemens Healthcare GmbH, Erlangen (DE); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 307 days.

(21) Appl. No.: 16/587,789

(22) Filed: Sep. 30, 2019

(65) Prior Publication Data

US 2021/0093266 A1 Apr. 1, 2021

(51) Int. Cl.
*A61B 6/00* (2006.01)
*G01N 23/046* (2018.01)
*A61B 6/03* (2006.01)
*G06T 11/00* (2006.01)
*A61N 5/10* (2006.01)

(52) U.S. Cl.
CPC ............ *A61B 6/4417* (2013.01); *A61B 6/037* (2013.01); *A61B 6/481* (2013.01); *G01N 23/046* (2013.01); *G06T 11/005* (2013.01); *A61N 2005/1098* (2013.01); *G01N 2223/3303* (2013.01); *G01N 2223/6126* (2013.01)

(58) Field of Classification Search
None
See application file for complete search history.

(56) References Cited

U.S. PATENT DOCUMENTS

2007/0167716 A1* 7/2007 Kinahan ................ A61B 6/405
600/407
2012/0070057 A1* 3/2012 Zhang ................... G06T 11/005
382/131

(Continued)

OTHER PUBLICATIONS

Kinahan, Paul E., et al. "Attenuation correction for a combined 3D PET/CT scanner." Medical physics 25.10 (1998): 2046-2053.

(Continued)

*Primary Examiner* — Hoon K Song

(57) ABSTRACT

A virtual 511 KeV attenuation map is generated from CT data. Spectral or multiple energy CT is used to more accurately extrapolate the 511 KeV attenuation map. Since spectral or multiple energy CT may allow for material decomposition and/or due to additional information in the form of measurements at different energies, the modeling used to generate the 511 KeV attenuation map may better account for all materials including high density material. The extrapolated 511 KeV attenuation map may more likely represent actual attenuation at 511 KeV without requiring extra scanning using a 511 KeV source external to the patient. The virtual 511 KeV attenuation map (e.g., CT data at 511 KeV) may provide more accurate PET image reconstruction.

17 Claims, 2 Drawing Sheets

(56) References Cited

U.S. PATENT DOCUMENTS

| | | | |
|---|---|---|---|
| 2015/0057535 A1* | 2/2015 | Sitek | G06T 11/005 600/426 |
| 2015/0117733 A1* | 4/2015 | Manjeshwar | G06T 11/005 382/131 |
| 2016/0228056 A1* | 8/2016 | Hooker | A61B 6/507 |
| 2017/0024634 A1* | 1/2017 | Miao | G06K 9/6277 |
| 2019/0066341 A1* | 2/2019 | Feng | A61B 6/5205 |
| 2020/0093451 A1* | 3/2020 | Nett | A61B 6/545 |
| 2021/0019924 A1* | 1/2021 | Moriyasu | G06T 7/70 |

OTHER PUBLICATIONS

Schmitz, Ruth E., et al. "The physics of PET/Ct scanners." PET and PET/CT: a clinical guide 3 (2005).

Zaidi, Habib, and Bruce Hasegawa. "Determination of the attenuation map in emission tomography." Journal of Nuclear Medicine 44.2 (2003): 291-315.

\* cited by examiner

SPECTRAL CT-BASED 511 KEV FOR POSITRON EMISSION TOMOGRAPHY

BACKGROUND

The present embodiments relate to positron emission tomography (PET). In PET, an unstable radionuclide emits a positron, which collides with an electron resulting in annihilation of mass and emission of energy in form of two photons (gamma radiation) with 511 KeV energy. The PET image acquisition is based on almost-simultaneous detection of these two photons, which creates a detected event along a line of response (LOR). These registered LORs are used for image reconstruction.

PET imaging, as compared to the single photon imaging, allows for absolute quantification of activity, a prerequisite of accurate PET quantification metrics (e.g., SUV or kinetic modeling parameters like Ki and flux measurement). For more accurate imaging and/or quantification, the attenuation of the photons through tissue is accounted for in reconstruction. The degree of attenuation is related to a cumulative attenuation coefficient of tissue across the LOR. To address attenuation, early generations of PET scanners utilized an external source of positron emissions moved around an exterior of the patient in order to acquire a "transmission image." An attenuation-corrected image is generated using this transmission image measured at 511 KeV. This "511 KeV transmission image" was the "attenuation map" for PET image reconstruction.

With the advent of PET with computed tomography (CT), the structural information of low-dose CT helped accurate localization of tracer distribution and avidity. In addition, this low-dose CT data is utilized as a substitute for the transmission image, avoiding having to maintain the extra source and subjecting the patient to creation of the transmission image. The 511 KeV attenuation map is extrapolated from the CT data using a simple bilinear mapping. However, information for the PET emission energy is inaccurate as the CT data is at a lower energy (e.g., polychromatic photon source with a range of energy below 100 KeV), and bilinear mapping is overly simple, resulting in less precision in quantification. This surrogate attenuation map has a high fidelity in many conditions, and the induced error of quantification may be relatively negligible in some situations. The error is not desired in any situation. There are circumstances in which the error becomes more prominent, such as measurements near high density material (e.g., bone, inserted objects, and/or contrast agents). The high-density material introduces bias in the extrapolated attenuation map due to scatter and beam-hardening.

SUMMARY

By way of introduction, the preferred embodiments described below include methods, systems, and non-transitory computer readable media for generating a virtual 511 KeV attenuation map from CT data. Spectral or multiple energy CT is used to more accurately extrapolate the 511 KeV attenuation map. Since spectral or multiple energy CT may allow for material decomposition and/or due to additional information in the form of measurements at different energies, the modeling used to generate the 511 KeV attenuation map may better account for all materials including high density material. The extrapolated 511 KeV attenuation map may more likely represent actual attenuation at 511 KeV without requiring extra scanning using a 511 KeV source external to the patient. The virtual 511 KeV attenuation map (e.g., CT data at 511 KeV) may provide more accurate PET image reconstruction.

In a first aspect, a method is provided for attenuation correction in positron emission tomography. A computed tomography (CT) scanner acquires spectral CT data for a patient. A 511 KeV attenuation map is generated from different energies of the spectral CT data. A positron emission tomography (PET) scanner acquires PET data along lines-of-response from emissions. An image of the patient is reconstructed from the PET data. The reconstructing is a function of the 511 KeV attenuation map. The image is displayed.

In one embodiment, the spectral CT data is acquired with a dual energy detector for detecting the spectral CT data detected at two different energies below 200 KeV. In another embodiment, the spectral CT data is acquired with a photon counting detector for detecting at three or more different energies below 200 KeV.

Various modeling may be used to generate the 511 KeV attenuation map from the spectral CT data at different energies. For example, a machine-learned model generates the 511 KeV attenuation map in response to input of the spectral CT data. The machine-learned model may be a convolutional neural network or other machine learning architecture. As another example, an analytical model-based simulation of tissues of the patient using material decomposition generates the 511 KeV attenuation map from the spectral CT data. In another example, a generalized linear model is used. In yet another example, a model (e.g., computational model) tuned based on comparison to information from a ground truth 511 KeV map is used.

The 511 KeV attenuation map is generated in a projection domain or an image domain. In either domain, the PET data altered to account for attenuation at 511 KeV. The altered PET data is used to reconstruct the emissions in object or image space. A PET image with or without other information (e.g., CT image) is displayed.

In a second aspect, a system is provided for positron emission tomography imaging. An x-ray scanner is configured to obtain attenuations at different energies for a patient volume. Rings of detectors spaced axially are operable to perform a positron emission tomography (PET) scan. A processor is configured to estimate attenuation at 511 KeV from the attenuations at the different energies and to generate a PET image from the PET scan using the attenuation at 511 KeV.

In one embodiment, the x-ray scanner is a dual energy or photon counting computed tomography scanner. The different energies are below 200 KeV, such as being below 100 KeV.

In another embodiment, the processor is configured to estimate the attenuation at 511 KeV in a projection domain. In other embodiments, the attenuation is estimated in the image or object domain.

Various models may be used to estimate the attenuation at 511 KeV. For example, a model optimized based on known 511 KeV attenuation is used. As another example, a machine-learned model is used to output the attenuation in response to input of the attenuations at the different energies.

Any images may be generated. For example, the processor is configured to generate the PET image from detected emissions of the PET scan corrected using the attenuation at 511 KeV.

In a third aspect, a non-transitory computer readable storage medium has stored therein data representing instructions executable by a programmed processor for attenuation correction in positron emission tomography (PET). The storage medium includes instructions for: estimating attenuation at a first energy from computed tomography data at second and third energies; correcting measured emissions for attenuation from the estimated attenuation at the first energy; and generating a PET image from the corrected measured emissions.

In a further embodiment, the instructions for estimating includes estimating the attenuation where the first energy is 511 KeV and the second and third energies are different energies below 200 KeV. The attenuation at 511 KeV is estimated from a model fit to the computed tomography data at the second and third energies for a patient.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

For PET imaging based on attenuation from CT, spectral CT is used to generate virtual 511 KeV CT as the attenuation map. A more accurate attenuation map is generated for PET reconstruction from spectral CT. By applying material decomposition methods using at least 2 different energy sets based on quantitative or other PET images, a monoenergetic (e.g. 511 KeV) map is used to correct PET data. The more accurate attenuation at the energy of the PET emissions is provided as compared to transformation techniques using CT data from a polychromatic photon source.

The spectral CT information may be acquired from a photon counting detector, dual energy detector, or other approaches. Since spectral CT or CT data at multiple energies is acquired, the estimated attenuation map at the energy of the PET emissions has less beam hardening effects, improved spatial resolution of CT images, results in a more accurate quantitative CT, allows for dose reductions of x-ray radiation, has improved contrast at lower energy photons, and has no septa for generating a three-dimensional attenuation map. The performance indices of CT have improved with spectral energy and particularly photon counting technology. This improvement allows for a more accurate attenuation map estimated for 511 KeV.

Since spectral CT may be used to better deal with estimating attenuation at 511 KeV for a broader range of materials, PET imaging is improved for situations where denser materials and/or materials having attenuation ambiguity are in the field of view. For example, improved PET images are provided for hip prosthesis infection evaluation, prosthetic aortic valve infection evaluation, left ventricular assist device infection evaluation, blood pool background quantification in the setting of contrast enhanced CT, quantification errors caused by enteric contrast, quantification errors caused by IV contrast in oncologic patients, or other situations.

Figure 1:
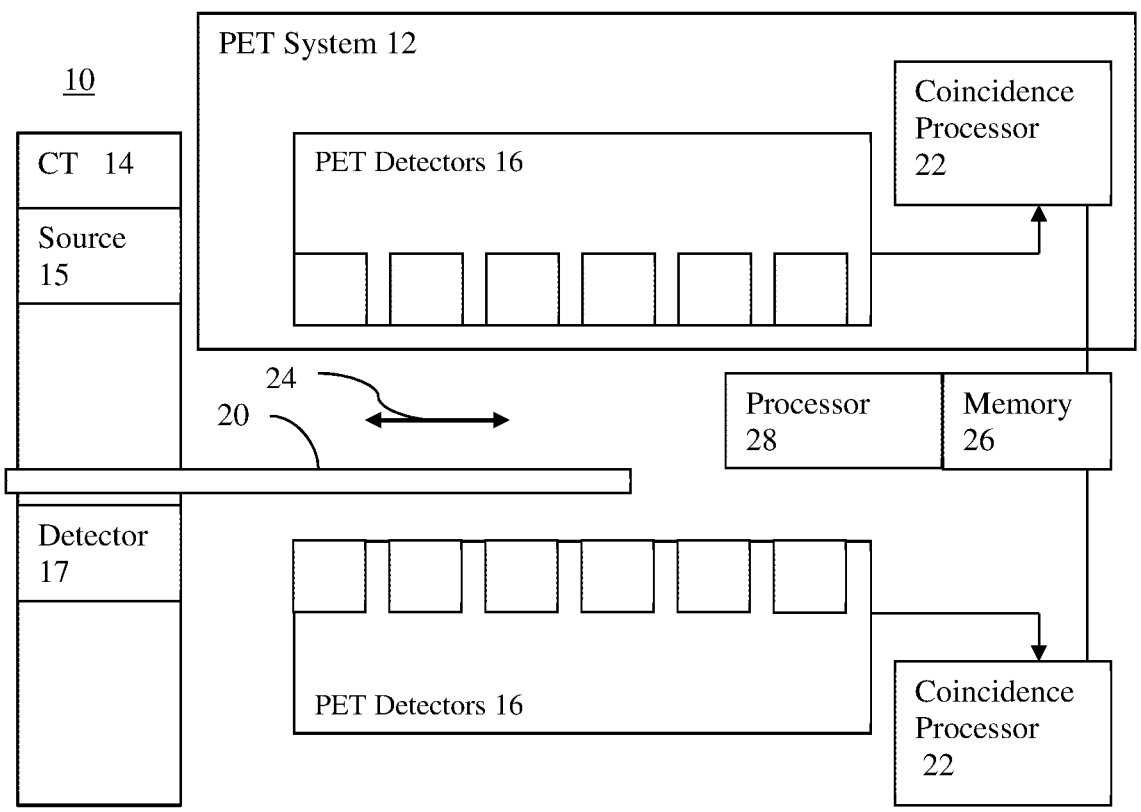
FIG. 1 is a block diagram of a system, according to one embodiment, for PET imaging using spectral CT for attenuation correction.

FIG. 1 shows one embodiment of a system for positron emission tomography imaging. The system is a combined PET-CT system 10 where CT is used for attenuation correction and for structural information in reconstruction for localization of activity concentration. Any PET-CT system 10 may be used. Spectral CT is used for the attenuation correction.

The PET-CT system 10 includes a CT scanner 14 and PET system 12. The PET system 12 includes rings of detectors 16, a bed 20, coincidence processors 22, a memory 26, and an image processor 28. The processor 28, memory 26, and/or a display are part of the PET system 12 or are separate (e.g., a computer or workstation). Additional, different, or fewer components may be provided. For example, the system is a computer without the detectors 16 and bed 20, instead relying on data acquired by a separate scanner. As another example, the PET-CT system 10 includes power supplies, communications systems, and user interface systems.

The CT system 14 includes an x-ray source 15 and opposing detector 17 mounted in a gantry. The CT system 14 is an x-ray scanner configured to obtain attenuation data for a patient volume. The gantry moves the source 15 and detector 17 about the patient for scanning. The processor 28 or a different processor computes the attenuation of the x-rays at different voxels within the scan volume. Any now known or later developed CT system 14 may be used. Other x-ray scanners, such as a CT-like C-arm scanner, may be used.

The CT system 14 is within a same housing as the PET system 12 or is spaced apart by and connected by a common track for the bed 20. Completely separate CT system 14 and PET system 12 may be used.

The CT system 14 is an x-ray scanner configured to obtain attenuations at different energies for the patient volume. Spectral CT data is obtained. For example, the detector 17 is a photon counting detector or a dual energy detector (e.g., dual layer) for detecting X-rays at different energies. As another example, the source 15 is a dual source or programmable source (e.g., kV switching) providing X-rays at different energies. The detector 17 detects the X-rays from the different transmission energies sequentially. In yet another example, spectral filtering for the source 15 and/or the detector 17 is used. Combinations of these approaches may be used. Spectral CT data representing X-ray attenuation at two or more different energies (e.g., different energy bands and/or different center or primary energy levels) is acquired by the CT system 14.

The spectral CT data is acquired in response to different transmit and/or receive energies. Any number of different energies and corresponding frames or sets of CT data may be acquired, such as two for dual energy or two or more for photon counting. In one embodiment, the different energies based on a dual energy detector are 90 KeV and 150 KeV. Other combinations may be provided, such as 90 KeV and 125 KeV. The different energies are all below 200 KeV, but higher energies may be used.

Different materials may have a same attenuation of X-rays at a given energy, such as calcium and iodine at a typical X-ray polychromatic photon source with a range of energy below 100 KeV. As a result, the attenuation for 511 KeV is mapped the same in bilinear extrapolation despite being different. A given material absorbs X-rays by different amounts for different energies, so the different materials may have different combinations of attenuations at different energies. The combination of attenuations in spectral CT may allow distinguishing between materials. This material decomposition may be used to better predict the attenuation at any given energy, such as at 511 KeV, for a material. The estimation may be provided based on the CT data at different energies without identifying the particular material and/or may be based on using spectral CT to identify the different materials.

The bed 20 is a gurney, table, or other support to hold an examination subject, such as a patient. A robot, gears, cable, track, and/or other device may move the bed 20. The movement is along an axial dimension represented by double arrow 24. The detectors 16 and/or PET scanner 10 form a bore or hollow cylinder through which the bed 20 moves the patient. The distance from the axial axis is the radial distance. The angle about the axial axis is the azimuth. Other coordinate systems, such as a cylindrical or polar coordinate system, may be used. One or more different stationary bed positions or continuous bed motion may be used to scan the patient for PET emissions.

The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

Figure 2:
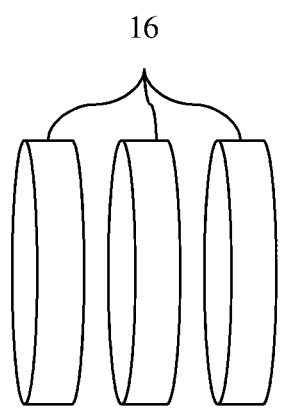
FIG. 2 shows example rings of detectors.

The detectors 16 are arranged individually or in groups. Blocks or groups of detectors 16 are arranged in any pattern around the bore. FIG. 2 represents blocks of detectors 16 arranged as separate rings around the bore. The rings are shown spaced apart but are placed adjacent or abutting each other. Any gap may be provided between blocks within a ring, detectors within a block, and/or between rings. Any number of detectors in a block (e.g., 8 or 16), detector blocks in a ring, and/or rings may be used. The rings may extend completely or only partially around the bore.

The PET system 12 is a nuclear imaging system. The detectors 16 detect gamma rays emitted indirectly by a positron-emitting tracer. Pairs of gamma rays generated by a same positron annihilation event may be detected using the same ring of the detectors 16. The pairs of gamma rays travel about 180 degrees apart. If the direction of travel intersects the arrangement of detectors 16 at two locations, a coincident pair may be detected. To distinguish specific pairs, the coincidence of detected gamma rays is determined. The timing of receipt is used to pair the detected gamma rays. The timing, as prompt data, may also indicate the time of flight (TOF), providing information about where along a line of response the emission occurred.

Each individual detection output from the detectors 16 includes energy, position, and timing information. Alternatively, the detectors 16 output energy information and a receiving coincidence processor 22 determines the timing and position (e.g., based on port assignment or connections). The timing information is used to determine coincidence of detection by different detectors 16 by the coincidence processors 22 with or without also determining a general position along the LOR of the emission based on TOF. Pairs of gamma rays associated with a same positron emission are determined. Based on the detected event, a LOR is determined given the detectors involved in the detection of that event.

The detected events are passed to the memory 26 and/or processor 28. The processor 28 connects with the detectors 16, such as through the coincidence processors 22. The processor 28 also connects with the CT system 14 to receive attenuation and/or structural information.

The image processor 28 is a general processor, digital signal processor, graphics processing unit, application specific integrated circuit, field programmable gate array, artificial intelligence processor, digital circuit, analog circuit, combinations thereof, or other now known or later developed device for processing detected LOR events, generating attenuation maps, and/or reconstructing. The processor 28 is a single device, a plurality of devices, or a network. For more than one device, parallel or sequential division of processing may be used. Different devices making up the processor 20 may perform different functions, such as one processor for handling LOR emission information and attenuation information and another processor for reconstructing the object (i.e., patient). In one embodiment, the processor 28 is a control processor or other processor of the PET-CT system 10 or the PET system 12. In other embodiments, the processor 28 is part of a separate workstation or computer or part of the CT system 14.

The processor 28 operates pursuant to stored instructions to perform various acts described herein. The processor 28 is configured by software, design, firmware, and/or hardware to perform any or all of the acts of FIG. 3. The operation and configuration of the processor 28 is first described in general below. An example implementation is described in more detail in the following discussion of FIG. 3.

The processor 28 is configured to estimate attenuation at 511 KeV from the attenuations at the different energies. The attenuations at the different energies from the spectral CT are used to estimate the attenuation at the 511 KeV or other energy of the detected PET emissions. A virtual 511 KeV attenuation map is generated. Rather than directly measuring, such as with a transmission image formed from moving a source of 511 KeV emissions about a patient, spectral CT data is used to estimate the virtual 511 KeV attenuation map. Rather than using attenuation from one CT energy or band and bilinear extrapolation, spectral CT data providing more information about attenuation and materials is used to better estimate the virtual 511 KeV attenuation map.

The attenuation map is estimated in the projection domain. The attenuations along different LORs and/or for sinograms are estimated. In other embodiments, the attenuation is estimated in the image or object domain. The attenuation at each location (e.g., voxel) is estimated.

The processor 28 is configured to estimate based on modeling. The attenuations measured for different energies are used to model the attenuation at 511 KeV or other PET emission energy. For example, a computational model is optimized based on known 511 KeV attenuation given spectral CT data for the same volume (e.g., phantom or patient). The values for one or more parameters of the computational model are set to provide the known 511 KeV given the input spectral CT data. For a later patient, the optimized computation model is used to estimate the 511 KeV attenuations given the measured spectral CT data. The model may be fit to the patient, such as adjusting the values of one or more parameters or by input of the spectral CT data for the patient. The fit model is used to estimate the virtual 511 KeV attenuations. In another example, a machine-learned model, such as a convolutional neural network, outputs the 511 KeV attenuation estimates in response to input of the spectral CT data. In yet other examples, a simulation model, analytical model, or other model is used. For example, material decomposition is performed. The model indicates the attenuation at 511 KeV for each material, so the attenuations are estimated from the model based on material decomposition in response to input of the spectral CT data (i.e., CT data at different energies). Any linear or non-linear modeling relating measured spectral CT data to attenuations at 511 KeV or other PET emission energy may be used.

The processor 28 is configured to generate a PET image from the PET scan using the estimated attenuation at 511 KeV. The measured emissions are corrected for attenuation. The attenuation estimated at 511 KeV is used to correct the emission or PET data. The correction is performed as part of reconstruction. The PET is corrected in the projection domain (by LOR), and then the corrected PET data is iteratively reconstructed into the object or image domain. Alternatively, the PET data is reconstructed into the image or object domain, such as for each iteration, and then the PET data in the object domain is corrected for attenuation at 511 KeV.

The processor 28 is configured to reconstruct the activity distribution using TOF for detected emissions along the lines of response. Alternatively, TOF is not used. The structural information from CT data for one or multiple energies may be used in the PET reconstruction to localize activity.

The processor 28 is configured to generate a PET image from the detected emissions of the PET scan corrected using the estimated attenuations at 511 KeV. PET data representing a plane is mapped to display values. Alternatively, PET data representing a volume is three-dimensionally rendered to a two-dimensional display, such as with projection or surface rendering. The PET image may or may not include, overlay, or be displayed adjacent to a CT image representing the patient.

The detected events, LOR information (e.g., sinograms), time step, prompt data, attenuation information, reconstructed data, image, or other data is stored in the memory 26. The data is stored in any format. The memory 26 is a buffer, cache, RAM, removable media, hard drive, magnetic, optical, database, or other now known or later developed memory. The memory 26 is a single device or group of two or more devices. The memory 26 is part of the PET system 12 or a remote workstation or database, such as a PACS memory.

The memory 26 is additionally or alternatively a non-transitory computer readable storage medium with processing instructions. The memory 26 stores data representing instructions executable by the programmed processor 28 for attenuation correction in PET. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

For example, the instructions are for estimating attenuation at a first energy (e.g., 511 KeV or other PET emission energy) from CT data at second and third energies. CT data from more than two energies may be used, such as different energies below 200 KeV. The attenuation at 511 KeV is estimated from a model fit to the CT data at the different energies for a patient. The measured emissions are corrected for attenuation from the estimated attenuation at the first energy. A PET image is generated from the corrected measured emissions.

The PET system 12 may include a display. For example, the processor 28 reconstructs the patient or object being scanned from the LOR and attenuation data. The reconstruction is used for three-dimensional rendering, multi-planar reconstruction, or two-dimensional imaging of the function of the object or patient. The images are displayed on the display. The display is a CRT, LCD, plasma screen, projector, printer, or other output device for showing an image.

Figure 3:
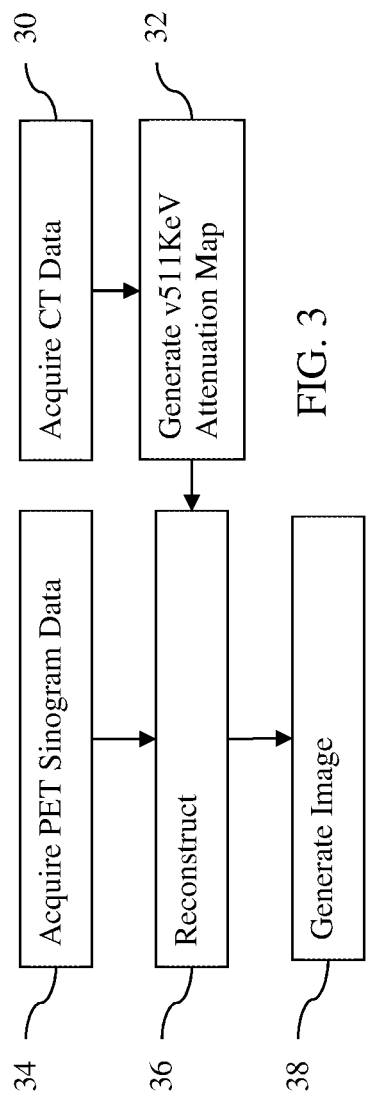
FIG. 3 is a flow chart of an embodiment of a method for attenuation correction in PET.

FIG. 3 shows a method for attenuation correction in PET. Photon-counting or other multiple energy CT is used to generate a virtual 511 KeV CT for PET image reconstruction. Attenuations measured for different energies using CT are used to estimate attenuation at the PET emission energy, allowing for more accurate attenuation correction especially where denser materials (e.g., contrast agents or inserted objects) and/or materials with similar attenuation at a typical CT energy level are in the scan volume.

The method of FIG. 3 is implemented by the processor 28, the PET system 12, the PET-CT system 10, the CT system 14, and/or other component or system. For example, the CT system 14 performs act 30, and the PET system 12 performs act 34. The image processor 28 (e.g., processor of the PET system 12) performs acts 36 and 38. The same or different processor (e.g., processor of the CT system 14) performs act 32. A display may be used for act 38. Other devices or components may be used instead or in addition to the imaging systems and/or processors.

Additional, different, or fewer acts may be performed. For example, act 38 is not performed. As another example, act 36 is not performed. The attenuation correction is applied without reconstruction.

The acts are performed in the order shown (numerical or top-to-bottom) or a different order. Acts 30 and/or 32 may be performed prior to, at a same time as, or after act 34.

In act 30, a CT scanner acquires attenuation information. A CT scan of the patient is performed by the CT scanner. Other scanners to measure the attenuation at different locations or along lines through the patient may be used. Alternatively, the attenuation information is acquired from memory, such as attenuation information from a previously performed CT scan.

The CT scan is of a volume of the patient. Any range of the patient may be scanned, such as from the hips to the neck. The entire patient may be scanned. The CT scan provides measures of attenuation of the x-ray energy at different locations, such as voxels, within the patient. The attenuations of the voxels are computed by tomography from a sequence of x-ray scans from different angles through the patient. The resulting CT intensity data represents voxels of the CT scan volume. Alternatively, the CT intensity data is projected along LORs to form CT intensities in the projection domain.

The CT scan is a spectral CT scan. Spectral CT data representing response to X-rays at different energies is acquired. For example, a dual energy detector is used to acquire CT data at two energies, such as 90 and 120 KeV. The energies are below 200 KeV or below 100 KeV, but other maximums may be provided. The energies are different than 511 KeV. As another example, the spectral CT data is acquired with a photon counting detector. The spectral CT data represents response to X-rays at two, three, four, or more different energies. Some or all of the different energies are below 200 KeV, 100 KeV, or other maximum. In other embodiments, dual source, spectral filtering on the source side, spectral filtering on the detector side, or kV switching are used to measure response to X-rays for different energies. Dual energy virtual non-contrast (VNC) and dual energy CT-based monoenergetic CT scans may be used to obtain dual energy information. Combinations of different approaches may be used, such as a dual source or kV switching with photon counting or a dual layer detector.

In act 32, an image processor generates a 511 KeV attenuation map from different the spectral CT data at different energies. A virtual or mutual monoenergetic image at 511 KeV, substantially 511 KeV (i.e., within 25 KeV of 511 KeV), or at or substantially at another PET energy is generated. By applying material decomposition methods or other modeling on quantitative images produced by spectral CT (i.e., quantitative CT data at two or more different energies), a monoenergetic (e.g., 511 KeV) map is created to correct for photon attenuation in PET. More accurate attenuation information is provided as compared to bilinear transformation from CT data for one energy or integrated over a range of energies.

The 511 KeV attenuation map is generated in the projection domain. Projection data is used to reconstruct the virtual 511 KeV attenuations. The CT data at different energies are used to determine the 511 KeV attenuation for each voxel. The 511 KeV attenuations for different voxels are integrated to find attenuations along LOR or emission projections. In another embodiment, the CT data at the different energies are projected or transformed into the projection domain. The 511 KeV attenuations are then estimated in the projection domain. The virtual 511 KeV attenuations in the projection domain are then used for PET reconstruction.

In an alternative embodiment, 511 KeV attenuation map is generated in the image domain. The CT datasets for the respective energies represent different voxels in the image domain. The virtual 511 KeV attenuations are estimated for the different voxels. Reconstructed photon-counting or other spectral CT data are used for reconstruction in PET.

The attenuation at 511 KeV is estimated from the attenuations at multiple other energies. A model relates the attenuations at the different energies to attenuation at 511 KeV. Various types of modeling may be used.

In one embodiment, a generalized linear model is used. The model is developed to map energy-binned images into a 511 KeV output. Many samples are provided to create a statistical model, such as a multivariate regression model. The relationship of CT data at different energies to CT data at 511 KeV is modeled.

In another embodiment, an analytical model-based simulation of tissues of the patient using material decomposition from the spectral CT data is used. The material composition is determined from the spectral CT data. The model then maps known or assigned attenuation values at 511 KeV from the material (e.g., tissue or object) for each location.

A parameterized model may be used. Ground truth data, such as many samples (e.g., tens, hundreds, or thousands) of known 511 KeV attenuation maps and respective CT measurements at the different energies are gathered. The known 511 KeV attenuation maps may be created by physics simulation or measurement of a transmission image (i.e., placing a 511 KeV source (e.g., Cesium source) adjacent a patient to measure). The model parameters are tuned or set based on the ground truth data and the respective CT measurements at the different energies. The settings of the parameters of the model are optimized using the samples. For example, the model is used to generate a virtual 511 KeV attenuation map, which is then compared to the ground truth. Voxel-wise comparison with 68Ge-based attenuation map, voxel-wise comparison with 137Cs-based attenuation map, and/or voxel-wise comparison with low-dose CT-based attenuation map may be used. The settings are adjusted to minimize the difference between the model produced attenuation maps and the ground truth attenuation maps.

In another approach for a parameterized model, the effect of the attenuation-map correction is evaluated or optimized. The comparison is of PET reconstruction after attenuation correction, such as comparing PET quantitative measures. Voxel-wise comparison is performed for two PET images reconstructed using low-dose CT-based attenuation map, $X_{CT}$, and the ground truth 511 KeV attenuation map (e.g., transmission image from 68Ge-$X_{Ge}$). The difference is used in optimization (i.e., minimize the difference). For example, the percentage difference is minimized, as represented by:

$$\% \; Diff = \frac{X_{CT} - X_{Ge}}{X_{Ge}} \times 100$$

The optimized parameterized model is then applied for a given patient. The model receives as input the CT attenuations at the different energies measured for a patient. This fits the model to the patient. Based on the optimized settings, the parameterized model outputs the 511 KeV attenuation.

In yet another embodiment, the 511 KeV attenuation map is generated by a machine-learned model in response to input of the spectral CT data. The samples of CT measurements and ground truth 511 KeV attenuation maps are used as training data in machine learning. The machine learns to generate the 511 KeV attenuation in response to input of the CT measurements at different energies. Convolutional neural network, image-to-image, encoder-decoder, U-Net, DenseNet, or other machine learning architectures and processes may be used. The machine-learned model is trained to output attenuation at 511 KeV for a voxel given input of CT attenuations at multiple other energies for the voxel with or without information from surrounding voxels. Alternatively, spatial distribution is used. The machine-learned model is trained to output an attenuation map for multiple or all voxels based on input of CT attenuations at the different energies for the multiple or all voxels. The machine-learned model may be trained to map energy-binned images into a virtual 511 KeV output attenuation map.

The attenuation map provides attenuation values by voxel or LOR. In reconstruction, the attenuation along the line is an integral of the attenuations of the line. The attenuation information is converted into attenuation coefficient factors (ACFs) for the LORs. For voxels, the attenuations values are attenuation coefficients.

In act 34, the PET scanner acquires PET data along LORs from emissions within the patient. PET sinogram data is acquired. Time of flight (TOF) data for emissions detected along a plurality of LORs may be acquired. The acquisition is by scanning with the PET scanner with a plurality of detectors. In alternative embodiments, the acquisition is by transfer or upload from a memory.

Gamma rays are detected by one or more rings of detectors or other grouping of detectors. The patient ingests or is injected with a radiopharmaceutical. The radiopharmaceutical includes an isotope. The isotope decays over time, resulting in generation of a positron. LOR events from a patient are detected from emissions of photons upon annihilation of the positron.

The acquisition occurs over any period. For example, the acquisition is over 1, 10, 100, or other number of minutes. The PET scanning acquires detected emission events for functional information. The detected gamma rays are checked for coincidence. Where TOF is used, the time difference or relative timing for coincident detections is recorded as prompt data. Any time window may be used for coincidence processing, such as 0.2 microsecond coincidence time window. Each detected emission event corresponds to a line or part of a line through a patient. By detecting emission events from different angles around a patient, a volume may be reconstructed.

In act 36, the image processor reconstructs an image of the patient from the PET data. For example, the image of the patient is reconstructed from the TOF data for the LORs and the attenuations. The image may be voxels, pixels, or other values that may be used to generate a display image (i.e., information in the object domain). The image or object space is reconstructed. The activity distribution in three-dimensions is reconstructed. The activity distribution is used for imaging, such as volume rendering, multi-planar reconstruction, or planar imaging.

Any reconstruction may be used. In one embodiment, the reconstruction is a Poisson iterative reconstruction, such as a maximum likelihood reconstruction. OSEM, FORE, or other reconstructions may be used. The reconstruction estimates the object or patient space from the PET data of the LORs. The detected events are used to iteratively determine the object space using forward, backward, or forward and backward projection.

The reconstruction is a function of the 511 KeV attenuation map. The reconstruction accounts for the attenuation using ACFs, attenuation coefficients, or other attenuation values for the LORs or voxels. The PET data is altered based on the 511 KeV attenuation map. The amplitude of the PET data is changed (e.g., increased) to account for the amount of attenuation by the tissue and/or objects through which the photon passed. The alteration may be in the projection domain, such as to start reconstruction. The altered PET data is used for reconstruction. The alteration may be in the image domain, such as applied in object space in one or more iterations of the reconstruction. The altered PET data is used to determine changes in distribution in the object space for further iterations transforming between the projection and image spaces. In one embodiment, the objective function for the reconstruction makes use of attenuation information. The alteration may be to an output of the reconstruction.

In act 38, an image is displayed. The reconstructed activity or emission distribution is used to create a PET image. The image is formed from reconstructing the object space and then rendering or imaging from the reconstructed object. The image is of the patient, such as a PET image showing function or uptake of the radiopharmaceutical. The image benefits from attenuation correction using accurate attenuation at 511 KeV of the PET emissions.

The image is rendered, such as three-dimensional rendered, from the voxels of the reconstruction to a two-dimensional display image. Alternatively, multi-planar reconstruction or planar imaging uses data representing a plane or planes in the reconstructed object to generate a two-dimensional image for the two-dimensional display.

The PET image may be displayed with a CT image. For example, a CT image is generated from the same view point, field of view, and/or rendered volume as the PET image. The images may be displayed adjacent to each other. Alternatively, the PET image is color mapped and overlaid on or combined with the CT image. Any spectral CT imaging may be used. Alternatively, the CT image is generated from the CT data for one of the energies.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for attenuation correction in positron emission tomography, the method comprising:
   acquiring, with a computed tomography (CT) scanner, spectral CT data for a patient;
   generating a virtual 511 KeV attenuation map in an image domain or a projection domain from different energies of the spectral CT data;
   acquiring, with a positron emission tomography (PET) scanner, PET data along lines-of-response from emissions;
   reconstructing an image of the patient from the PET data, the reconstructing being a function of the virtual 511 KeV attenuation map; and
   displaying the image.

2. The method of claim 1 wherein acquiring the spectral CT data comprises acquiring with a dual energy detector, the spectral CT data detected at two different energies below 200 KeV.

3. The method of claim 1 wherein acquiring the spectral CT data comprises acquiring with a photon counting detector, the spectral CT data detected at three or more different energies below 200 KeV.

4. The method of claim 1 wherein generating comprises generating the virtual 511 KeV attenuation map by a machine-learned model in response to input of the spectral CT data.

5. The method of claim 4 wherein generating comprises generating by the machine-learned model comprising a convolutional neural network.

6. The method of claim 1 wherein generating comprises generating with an analytical model-based simulation of tissues of the patient using material decomposition from the spectral CT data.

7. The method of claim 1 wherein generating comprises generating with a generalized linear model.

8. The method of claim 1 wherein generating comprises generating the virtual 511 KeV attenuation map from a model tuned based on comparison to information from a ground truth 511 KeV map.

9. The method of claim 1 wherein reconstructing comprises altering the PET data based on the virtual 511 KeV attenuation map and reconstructing from the altered PET data.

10. The method of claim 1 wherein displaying the image comprises displaying a PET image.

11. A system for positron emission tomography imaging, the system comprising:
an x-ray scanner configured to obtain attenuations at different energies for a patient volume;
rings of detectors spaced axially operable to perform a positron emission tomography (PET) scan; and
a processor configured to generate a virtual attenuation map at 511 KeV from the attenuations at the different energies and to generate a PET image from the PET scan using the virtual attenuation map in an image domain or a projection domain at 511 KeV.

12. The system of claim 11 wherein the x-ray scanner comprises a dual energy or photon counting computed tomography scanner, and wherein the different energies are below 200 KeV.

13. The system of claim 11 wherein the processor is configured to estimate the virtual attenuation map at 511 KeV from a model optimized based on known 511 KeV attenuation.

14. The system of claim 11 wherein the processor is configured to estimate the virtual attenuation map at 511 KeV from a machine-learned model in response to input of the attenuations at the different energies.

15. The system of claim 11 wherein the processor is configured to generate the PET image from detected emissions of the PET scan corrected using the virtual attenuation map at 511 KeV.

16. A non-transitory computer readable storage medium having stored therein data representing instructions executable by a programmed processor for attenuation correction in positron emission tomography (PET), the storage medium comprising instructions for:
estimating a virtual attenuation map in a projection domain at a first energy from computed tomography data at second and third energies;
correcting measured emissions for attenuation from the estimated attenuation at the first energy; and
generating a PET image from the corrected measured emissions.

17. The non-transitory computer readable storage medium of claim 16 wherein estimating comprises estimating the attenuation where the first energy comprises 511 KeV and the second and third energies are different energies below 200 KeV, the attenuation at 511 KeV estimated from a model fit to the computed tomography data at the second and third energies for a patient.

* * * * *